United States Patent [19]

Rovnyak

[11] 4,220,791
[45] Sep. 2, 1980

[54] MERCAPTOACYLPYRAZOLIDINONE CARBOXYLIC ACID DERIVATIVES

[75] Inventor: George C. Rovnyak, Hopewell, N.J.

[73] Assignee: E. R. Squibb & Sons, Inc., Princeton, N.J.

[21] Appl. No.: 18,547

[22] Filed: Mar. 8, 1979

[51] Int. Cl.$^2$ .......................................... C07D 231/08
[52] U.S. Cl. .................................. 548/367; 424/273 P
[58] Field of Search ......................................... 548/367

[56] References Cited

U.S. PATENT DOCUMENTS

| 3,153,654 | 10/1964 | Ficken et al. | 548/367 |
| 4,095,024 | 6/1978 | Fleming et al. | 548/367 |
| 4,105,776 | 8/1978 | Ondetti et al. | 548/367 |
| 4,129,566 | 12/1978 | Ondetti et al. | 546/326 |

FOREIGN PATENT DOCUMENTS 861454 6/1978 Belgium .

Primary Examiner—Natalie Trousof
Assistant Examiner—Jane T. Fan
Attorney, Agent, or Firm—Lawrence S. Levinson; Donald J. Barrack

[57] ABSTRACT

Compounds having the formula

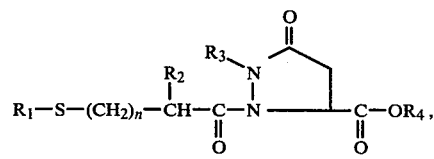

and basic salts thereof, wherein $R_1$ is hydrogen, alkyl, aryl, arylalkyl or

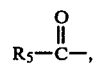

wherein $R_5$ is alkyl or aryl;
$R_2$ is hydrogen or alkyl;
$R_3$ is hydrogen, alkyl, aryl or arylalkyl; and
$R_4$ is hydrogen, alkyl, or arylalkyl;

have useful hypotensive activity.

22 Claims, No Drawings

MERCAPTOACYLPYRAZOLIDINONE CARBOXYLIC ACID DERIVATIVES

RELATED APPLICATIONS

United States patent application, Ser. No. 18,548, filed Mar. 8, 1979 discloses mercaptoacyl dihydropyrazole carboxylic acid derivatives.

BACKGROUND OF THE INVENTION

U.S. Pat. No. 4,105,776, issued Aug. 8, 1978 describes a group of thioalkanoyl derivatives of azetidine-, pyrrolidine- and piperidinecarboxylic acid compounds having the structural formula $$R_a-S-(CH)_n-\underset{R_b}{CH}-\underset{\underset{O}{\|}}{C}-N-\underset{\underset{CH-COR_e}{|}}{\overset{R_c}{\underset{|}{C}}}\underset{H_2C-(CH)_m}{\overset{R_d}{\underset{|}{}}}$$

wherein the symbols can be, inter alia, as follows: $R_a$ can be hydrogen, lower alkyl, phenyl, substituted phenyl, phenyl-lower alkyl, lower alkyl—$\overset{O}{\underset{\|}{C}}$—, phenyl—$\overset{O}{\underset{\|}{C}}$— or phenyl-lower alkyl—$\overset{O}{\underset{\|}{C}}$—, $R_b$ can be hydrogen, $R_c$ can be hydrogen or lower alkyl, $R_d$ can be hydrogen, hydroxy or lower alkyl, $R_e$ can be hydroxy, —$NH_2$ or lower alkoxy, n can be 0, 1 or 2 and m can be 1, 2 or 3.

U.S. Pat. No. 4,129,566, issued Dec. 12, 1978, describes derivatives of dehydrocyclicimino acids having the structural formula $$R_f-S-(CH_2)_n-\underset{|}{\overset{R_c}{CH}}-\underset{\underset{O}{\|}}{C}-N\underset{\underset{COOR_g}{|}}{\overset{H_2C}{\underset{|}{\overset{H}{\underset{|}{C}}}}}\underset{CH_2}{\overset{CH}{\underset{\|}{}}}$$

wherein the symbols can be, inter alia, as follows: $R_c$, $R_f$ and $R_g$ can each be hydrogen or lower alkyl and n can be 0 or 1.

Belgian Pat. No. 861,454, published June 2, 1978, describes compounds having the structural formula $$R_h-S-(CH_2)_p-\underset{|}{\overset{R_i}{CH}}-\underset{\underset{O}{\|}}{C}-N\underset{\underset{|}{(R_j-CH)_m}}{\overset{X}{\underset{}{}}}\underset{(CH-R_k)_n}{\underset{|}{}}\underset{\underset{O}{\|}}{CH}-\underset{\underset{O}{\|}}{C}-R_L$$

wherein the symbols can be, inter alia as follows: $R_h$ can be hydrogen, lower alkanoyl or benzoyl, $R_i$, $R_j$ and $R_k$ can each be hydrogen or lower alkyl, $R_L$ can be hydroxy or lower alkoxy, m can be 1, 2, or 3, n can be 0, 1, or 2 and m+n can be 2 or 3, p can be 0 or 1 and X can be O, S, SO or $SO_2$, m being 2 and n being 1 when X is O.

The compounds set forth above are disclosed as being useful as inhibitors of the conversion of the decapeptide angiotensin I to angiotensin II, and are, therefore, useful in reducing or relieving angiotensin related hypertension.

BRIEF DESCRIPTION OF THE INVENTION

Compounds having the formula $$R_1-S-(CH_2)_n-\underset{|}{\overset{R_2}{CH}}-\underset{\underset{O}{\|}}{C}-N\underset{}{\overset{R_3\underset{\|}{\underset{}{N}}\overset{O}{\underset{}{}}}{}}\underset{\underset{O}{\|}}{C}-OR_4,$$ I and basic salts thereof, have hypotensive activity. In formula I, and throughout the specification, the symbols are as defined below.

$R_1$ is hydrogen, alkyl, aryl, arylalkyl or $$R_5-\overset{O}{\underset{\|}{C}}-$$

wherein $R_5$ is alkyl or aryl;
$R_2$ is hydrogen or alkyl;
$R_3$ is hydrogen, alkyl, aryl, or arylalkyl;
$R_4$ is hydrogen, alkyl, or arylalkyl; and
n is 0, 1 or 2.

The term "aryl," as used through the specification either by itself or as part of a larger group, refers to phenyl or phenyl substituted with one, two or three halogen, alkyl, alkoxy, hydroxy, $$alkyl-\overset{O}{\underset{\|}{C}}-,$$

nitro, amino, alkylamino, dialkylamino, trifluoromethyl, cyano or carboxyl groups. Phenyl is the preferred aryl group.

The term "alkyl," as used throughout the specification either by itself or as part of a larger group, refers to groups having 1 to 8 carbon atoms. Alkyl groups having 1 to 3 carbon atoms are preferred.

The term "alkoxy," as used throughout the specification either by itself or as part of a larger group, refers to groups having 1 to 8 carbon atoms. Alkoxy groups having 1 to 3 carbon atoms are preferred.

The term "halogen," as used throughout the specification either by itself or as part of a larger group, refers to fluorine, chlorine, bromine and iodine. The preferred halogen groups are chlorine and bromine.

DETAILED DESCRIPTION OF THE INVENTION

The compounds of formula I are useful as hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiontensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen→(renin)→angiotensin I→(ACE)- →angiotensin II sequence by inhibiting angiotensin converting enzyme and reducing or eliminating the formation of the pressor substance angiotensin II. Thus by the administration of a composition containing one or a combination of compounds of formula I, angiotensin dependent hypertension in the species of mammal suffering therefrom is alleviated. A single dose, or preferably two to four divided daily doses, provided on a basis of about 0.1 to 100 mg. per kilogram of body weight per day, preferably about 1 to 50 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of formula I can be formulated for use in the reduction of blood pressure in compositions such as tablets, capsules or elixirs for oral administration or in sterile solutions or suspensions for parenteral administration. About 10 to 500 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of this invention can be obtained by reacting a 5-oxo-3-pyrazolidinecarboxylic acid having the formula

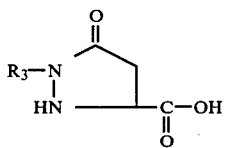

with a mercaptoacyl halide having the formula

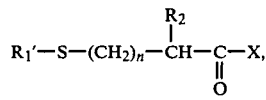

wherein $R_1'$ is alkyl, aryl, arylalkyl,

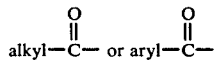

and X is chlorine or bromine to obtain the corresponding carboxylic acid products having the formula

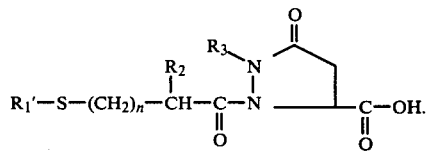

The reaction is preferably run in a two phase solvent system such as water/ether or water/ethyl acetate, in the presence of a base such as an alkali metal hydroxide or alkali metal carbonate. While reaction conditions are not critical, more favorable yields will be obtained if the reaction is run within the following parameters. The ratio of pyrazolidine derivative (formula II) to mercaptoacyl halide (formula III) will preferably be within the range of 1:1 to 1:2, most preferably within the range of 1:1 to 1:1.2. The temperature of the reaction is preferably maintained at about 0°–25° C., most preferably 0°–5° C. Additional base should be added as needed to maintain the pH of the reaction mixture between about 7.0 and 8.5.

Alternatively, a compound of formula IV can be obtained by reacting a 5-oxo-3-pyrazolidinecarboxylic acid of formula II with a mixed anhydride in place of the mercaptoacyl halide of formula III.

The compounds of formula I wherein $R_1$ and $R_4$ are both hydrogen can be prepared by deacylation of the corresponding compounds of formula IV wherein $R_1'$ is

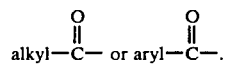

Hydrolysis of the thioacyl group can be accomplished by treatment with aqueous base, e.g., ammonium hydroxide or an alkali metal hydroxide.

The compounds of formula I wherein $R_4$ is alkyl or arylalkyl are obtained by treating the corresponding acid of formula I with the appropriate diazoalkane or with the appropriate alcohol in the presence of a dehydrating agent such as dicyclohexylcarbodiimide. Alternatively, an acid of formula I can be converted first to an acid halide and then reacted with the appropriate alcohol in the presence of an acid acceptor, e.g., an organic base such as triethylamine.

The compounds of this invention wherein $R_4$ is hydrogen form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic, physiologically acceptable salts are preferred, although other salts are also useful, e.g., in isolating or purifying the product.

The 5-oxo-3-pyrazolidinecarboxylic acids of formula II wherein $R_3$ is hydrogen or aryl can be prepared using the procedure set forth in German Offenlegungsschrift No. 2,603,400. As described therein, a maleic acid half ester is treated with an aryl hydrazine in an aqueous sodium carbonate medium to yield the corresponding compound of formula II wherein $R_3$ is aryl. It has been found that if hydrazine hydrate is substituted for aryl hydrazine the procedure will yield the corresponding compound of formula II wherein $R_3$ is hydrogen.

The 5-oxo-3-pyrazolidinecarboxylic acids of formula II wherein $R_3$ is alkyl or arylalkyl can be prepared from the corresponding compounds of formula II wherein $R_3$ is hydrogen. The nitrogen atom in the 2-position is first protected, e.g., with a benzyl or benzyloxycarbonyl group, the protected compound is next alkylated in the presence of a base, and the protecting group is next removed.

The mercaptoacyl halide derivatives of formula III are prepared by methods known in the art; see, for example Arkiv. Kimi. Mineral. Geol., 14A (7), 1940; J. Chem. Soc., 2016(1970); J.A.C.S., 69, 2328 (1947); and J.A.C.S., 69, 2334 (1947).

The compounds of formula I each contains at least one asymmetric carbon and accordingly exist in steroisomeric forms or in racemic mixtures thereof. The above-described syntheses can utilize the racemate or one of the enantiomers as starting material. When the racemic starting material is used in the synthetic procedure, the steroisomers obtained in the product can be separated by conventional fractional crystallization of the diastereomeric salt mixture formed, e.g., with an optically active amine. It is theorized that the activity of the racemic products is due mostly to the L-isomer with respect to the carbon of the amino acid, and this isomer is accordingly preferred.

The following examples are specific embodiments of this invention.

EXAMPLE 1

DL-2-[3-(Acetylthio)-1-oxopropyl]-5-oxo-1-phenyl-3-pyrazolidinecarboxylic acid (A) DL-5-Oxo-1-phenyl-3-pyrazolidinecarboxylic acid A solution of 50.0 g of maleic anhydride in 250 ml of methanol is heated at reflux temperature for 1 hour. Solvent is removed in vacuo, and the residual oil is dissolved in 250 ml of water and treated portionwise with 27.0 g of sodium carbonate. This solution is then treated with 55.0 g of phenyl hydrazine and heated at 90° C. for 9 hours. After cooling, the mixture is extracted twice with dichloromethane and then treated with 90 ml of 6 N hydrochloric acid (to pH 2.0), yielding 77.0 g of the title compound, melting point 197°–199° C.

Anal. Calcd. for $C_{10}H_{10}N_2O_3$: C,58.24; H,4.88; N, 13.58. Found: C,58,10; H,4.66; N,13.54.

(B) DL-2-[3-(Acetylthio)-1-oxopropyl]-5-oxo-1-phenyl-3-pyrazolidinecarboxylic acid A suspension of 17.6 g of DL-5-oxo-1-phenyl-3-pyrazolidinecarboxylic acid in 125 ml of distilled water is treated gradually with 4.7 g of sodium carbonate. The solution is layered with 40 ml of ethyl acetate, cooled to 5° C. and treated with 15.0 g of 3-(acetylthio)propionyl chloride. The pH of the mixture is maintained between 8.0 and 8.5 during the 5 minute addition period using a solution of 12 g of sodium carbonate in 50 ml of distilled water.

The mixture is stirred at room temperature for 10 minutes. The ethyl acetate layer is discarded and the aqueous layer is extracted two times with ethyl acetate. The pH of the aqueous layer is lowered to 2.2 using 44 ml of 6 N hydrochloric acid. Extraction of the oily product into ethyl acetate (two 100 ml portions) results in the isolation of 3.5 g of insoluble starting material. The combined soluble extracts are concentrated to approximately 75 ml and allowed to stand at room temperature for three hours, after which an additional 2.3 g of starting material is collected by filtration. The filtrate contains a mixture of starting material and product. Chromatography over silica gel using toluene and toluene/ethyl acetate fails to give a homogeneous product. The mixture obtained from this procedure (16 g) is dissolved in 50 ml of hot ethyl acetate and cooled for about 16 hours to yield 3.4 g of the title compound, melting point 144°–146° C.

Anal. Calcd. for $C_{15}H_{16}N_2O_5S$: C,53.55; H,4.79; N,8.33; S,9.52. Found: C,53.50; H,4.57; N,8.02; S,9.25.

EXAMPLE 2

DL-2-[3-(Acetylthio)-1-oxopropyl]-5-oxo-3-pyrazolidinecarboxylic acid (A) DL-5-Oxo-3-pyrazolidinecarboxylic acid A solution of 98.0 g of maleic anhydride in 500 ml of methanol is heated at reflux for one hour. The solvent is evaporated in vacuo and the residual oil is dissolved in 600 ml of water and treated gradually with 53 g of sodium carbonate. To this solution 52 g of hydrazine hydrate is added and the mixture is stirred and heated at 100° C. for 9 hours. The solution is concentrated to approximately one-half volume, and treated with 170 ml of 6 N hydrochloric acid to pH 1.9 to give 49.0 g of product, melting point 188°–190° C.

Anal. Calcd. for $C_4H_6N_2O_3$: C, 36.92; H, 4.64; N, 21.53. Found: C, 36.32; H, 4.53; N, 21.42.

(B) DL-2-[3-(Acetylthio)-1-oxopropyl]-5-oxo-3-pyrazolidinecarboxylic acid

Following the procedure of Example 1B, but substituting 12.0 g of DL-5-oxo-3-pyrazolidinecarboxylic acid for DL-5-oxo-1-phenyl-3-pyrazolidinecarboxylic acid and utilizing 16.4 g of 3-(acetylthio)propionyl chloride, yields 21.3 g of crude product, melting point 205°–207° C.

A solution of 4.35 g of the crude product in 20 ml of warm dimethylformamide is treated with a solution of 3.0 g of dicyclohexylamine in 75 ml of ethyl acetate to give 5.3 g of the salt, melting point 178°–180° C., dec. The salt is partitioned between 10% potassium hydrogen sulfate and ethyl acetate. An insoluble impurity (2 g, melting point >260° C.) is filtered off before the layers are separated. The ethyl acetate is dried over magnesium sulfate and evaporated to leave a glass-like solid. Trituration with ether yields 1.2 g of the title compound, melting point 150°–152° C.

Anal. Calcd. for $C_9H_{12}N_2O_5S$: C, 41.52; H, 4.64; N, 10.76; S, 12.31. Found: C, 41.80; H, 4.76; N, 11.06; S, 12.34.

EXAMPLE 3

DL-2-(3-Mercapto-1-oxopropyl)-5-oxo-3-pyrazolidinecarboxylic acid

DL-2-[3-(Acetylthio)-1-oxopropyl]-5-oxo-3-pyrazolidinecarboxylic acid (1.2 g) is treated in an argon atmosphere with 8 ml of a cold solution of 6.5 N ammonium hydroxide. After one hour at room temperature, the solution is extracted with ethyl acetate and treated with concentrated hydrochloric acid to pH 2. The water soluble product is extracted with five 20 ml portions of ethyl acetate. The combined extracts are dried over magnesium sulfate and evaporated to an oil which gradually solidifies. This material is dried in vacuo at 100° C. for 1 hour yielding 0.45 g of the title compound, melting point 140°–142° C.

Anal. Calcd. for $C_7H_{10}N_2O_4S$: C, 38.52; H, 4.61; N, 12.83; S, 14.69. Found: C, 38.60; H, 4.78; N, 12.99; S, 14.54.

EXAMPLES 4–9

Following the procedure of Example 1, but substituting the compound listed in column I for phenyl hydrazine and the compound listed in column II for 3-(acetylthio)propionyl chloride, yields the product listed in column III.

| | Column I | Column II |
|---|---|---|
| 4. | 4-chlorophenylhydrazine (NH₂—NH—C₆H₄—Cl) | CH₃—CH₂—C(O)—S—(CH₂)₂—CH(CH₃)—C(O)—Cl |
| 5. | 3-methylphenylhydrazine (NH₂—NH—C₆H₄—CH₃) | C₆H₅—C(O)—S—CH₂—CH(CH₂CH₃)—C(O)—Cl |
| 6. | 2-methoxyphenylhydrazine (NH₂—NH—C₆H₄—OCH₃) | CH₃—S—CH₂—C(O)—Cl |
| 7. | 2,4-dichlorophenylhydrazine (NH₂—NH—C₆H₃Cl₂) | C₆H₅—CH₂—S—CH₂—CH(CH₃)—C(O)—Cl |
| 8. | 3-trifluoromethylphenylhydrazine (NH₂—NH—C₆H₄—CF₃) | C₆H₅—S—(CH₂)₂—C(O)—Cl |
| 9. | 4-nitrophenylhydrazine (NH₂—NH—C₆H₄—NO₂) | CH₃—C₆H₄—CH₂—S—(CH₂)₂—CH(CH₃)—C(O)—Cl |

Column III

4. CH₃—CH₂—C(O)—S—(CH₂)₂—CH(CH₃)—C(O)—N(4-ClC₆H₄)—N(C(O)CH₂—)—CH(COOH) [succinic acid hydrazide derivative with 4-chlorophenyl]

5. C₆H₅—C(O)—S—CH₂—CH(CH₂CH₃)—C(O)—N(3-CH₃C₆H₄)—N(C(O)CH₂—)—CH(COOH)

6. CH₃—S—CH₂—C(O)—N(2-CH₃OC₆H₄)—N(C(O)CH₂—)—CH(COOH)

7. C₆H₅—CH₂—S—CH₂—CH(CH₃)—C(O)—N(2,4-Cl₂C₆H₃)—N(C(O)CH₂—)—CH(COOH)

-continued

8. 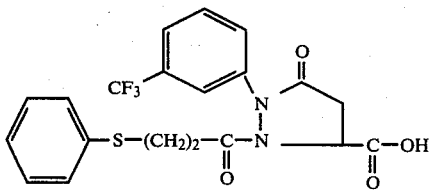

9. 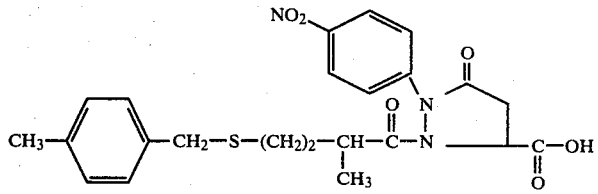

What is claimed is:
1. A compound having the formula

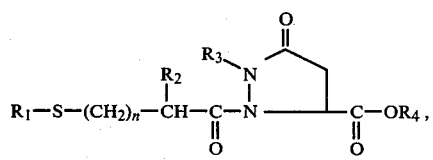

or a physiologically acceptable basic salt thereof, wherein $R_1$ is hydrogen, alkyl, aryl, arylalkyl or

wherein $R_5$ is alkyl or aryl;
$R_2$ is hydrogen or alkyl;
$R_3$ is hydrogen, alkyl, aryl or arylalkyl;
$R_4$ is hydrogen, alkyl, or arylalkyl; and
n is 0, 1 or 2;
wherein the term "aryl" refers to phenyl or phenyl substituted with one, two or three halogen, alkyl, alkoxy, hydroxy,

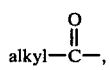

nitro, amino, alkylamino, dialkylamino, trifluoromethyl, cyano or carboxyl groups; and the terms "alkyl" and "alkoxy" refer to groups having 1 to 8 carbon atoms.

2. A compound in accordance with claim 1 wherein $R_1$ is hydrogen.

3. A compound in accordance with claim 1 wherein $R_1$ is alkyl.

4. A compound in accordance with claim 1 wherein $R_1$ is aryl.

5. A compound in accordance with claim 1 wherein $R_1$ is arylalkyl.

6. A compound in accordance with claim 1 wherein $R_1$ is

7. A compound in accordance with claim 1 wherein $R_2$ is hydrogen.

8. A compound in accordance with claim 1 wherein $R_2$ is alkyl.

9. A compound in accordance with claim 1 wherein $R_3$ is hydrogen.

10. A compound in accordance with claim 1 wherein $R_3$ is alkyl.

11. A compound in accordance with claim 1 wherein $R_3$ is aryl.

12. A compound in accordance with claim 1 wherein $R_3$ is arylalkyl.

13. A compound in accordance with claim 1 wherein $R_4$ is hydrogen.

14. A compound in accordance with claim 1 wherein $R_4$ is alkyl.

15. A compound in accordance with claim 1 wherein $R_4$ is arylalkyl.

16. A compound in accordance with claim 1 which is a basic salt.

17. A compound in accordance with claim 1 wherein n is 0.

18. A compound in accordance with claim 1 wherein n is 1.

19. A compound in accordance with claim 1 wherein n is 2.

20. The compound in accordance with claim 1, DL-2-[3-(acetylthio)-1-oxopropyl]-5-oxo-1-phenyl-3-pyrazolidinecarboxylic acid.

21. The compound in accordance with claim 1, DL-2-[3-(acetylthio)-1-oxopropyl]-5-oxo-3-pyrazolidinecarboxylic acid.

22. The compound in accordance with claim 1, DL-2-(3-mercapto-1-oxopropyl)-5-oxo-3-pyrazolidinecarboxylic acid.

* * * * *